United States Patent [19]

Claiborne et al.

[11] Patent Number: 4,890,478
[45] Date of Patent: Jan. 2, 1990

[54] GAS-IN-OIL MONITORING APPARATUS AND METHOD

[75] Inventors: C. Clair Claiborne, Sharpsville; Robert A. Kurz, Hermitage; Henry A. Pearce, Jr., Stoneboro; Harry R. Sheppard, Hermitage, all of Pa.

[73] Assignee: Westinghouse Electric Corp., Pittsburgh, Pa.

[21] Appl. No.: 95,745

[22] Filed: Sep. 11, 1987

[51] Int. Cl.⁴ ............................................. G01N 1/22
[52] U.S. Cl. ............................................. 73/19
[58] Field of Search ............... 55/16, 158; 73/19, 26, 73/27 R, 23, 863.23, 61 R; 422/98, 88; 338/34; 340/634; 324/62, 65 P

[56] References Cited

U.S. PATENT DOCUMENTS

| | | | |
|---|---|---|---|
| 3,666,460 | 2/1975 | Pearce | 73/19 |
| 3,676,820 | 7/1972 | Taguchi | 73/27 R X |
| 3,906,473 | 9/1975 | Le Vine | 340/634 |
| 3,973,848 | 8/1976 | Jowett et al. | 73/23 X |
| 4,012,692 | 3/1977 | Eicker | 422/98 |
| 4,058,373 | 11/1977 | Kurz | 55/16 |
| 4,402,211 | 9/1983 | Sugawara et al. | 73/19 |
| 4,444,040 | 4/1984 | Sakai et al. | 73/19 |
| 4,502,320 | 3/1985 | Sakai et al. | 73/19 |
| 4,542,640 | 9/1985 | Clifford | 73/23 |
| 4,567,475 | 1/1986 | Bukowiecki et al. | 73/23 |
| 4,587,834 | 5/1986 | Fisher | 73/23.1 |
| 4,627,269 | 12/1986 | Forster et al. | 73/23 |

FOREIGN PATENT DOCUMENTS 2064932 3/1987 Japan ................................. 55/158

Primary Examiner—Hezron E. Williams
Attorney, Agent, or Firm—Joyce L. Morrison

[57] ABSTRACT

An on-line gas-in-oil monitoring apparatus and method extracts certain reducing or combustible gases from oil and detects their presence and concentration substantially simultaneously using a sensor. The sensors are sintered metal oxide semi-conductors with adsorbed oxygen. The presence of a reducing or combustible gas proportionally increases the conductivity of the semi-conductor. Any resultant change in conductivity indicates the presence and concentraton of the reducing or combustible gas in the semi-conductor. After the analytical cycle the sensors are regenerated by exposure to oxygen.

19 Claims, 2 Drawing Sheets

GAS-IN-OIL MONITORING APPARATUS AND METHOD

BACKGROUND OF THE INVENTION

1. Field Of The Invention

This invention relates to an on-line gas-in-oil monitoring apparatus and method, and more particularly to a gas-in-oil monitoring apparatus which extracts certain reducing or combustible gases, such as hydrogen and carbon monoxide, from oil in a transformer or other electrical apparatus and detects the presence and concentration of these gases in the oil substantially simultaneously and subsequently regenerates the sensors.

2. Description Of The Prior Art

It is well known that the operating liquid insulated electrical apparatus, such as oil-filled power transformers can be ascertained by determining what gases and their concentration are dissolved in the insulating liquid. Certain gases such as carbon monoxide and carbon dioxide are given off and dissolved in transformer oil as a result of thermal aging and degradation of the cellulose insulation used in the transformer. Arcing in the transformer oil, energy sparked discharges and severe heating which cause decomposition of the oil, are known to produce larger percentages of hydrogen dissolved in the oil. In addition, large quantities of hydrogen indicate excessive moisture in critical areas of the transformer.

Oil and cellulose constitute the primary insulating components of transformers, therefore their decomposition is indicative of deterioration in the transformer. Analysis as to which gases and their concentration are dissolved in the oil can provide an indication of the status and condition of a transformer and the type and location of the problem. Periodic analysis of the transformer oil is used to determine the condition of the transformer. It is known to extract the gas from the oil in an electrical transformer, remove it from the transformer itself, and analyze it by chromatographic methods, See U.S. Pat. Nos. 4,587,834 and 4,058,373. U.S. Pat. No. 3,866,460, which is incorporated by reference, discloses an oil-in-gas monitor which detects the amount of a predetermined gas-in-oil in an electrical apparatus by measurement of the partial pressure of the hydrogen gas.

There remains a need for an on-line gas-in-oil monitoring apparatus and method that automatically extracts gases from the oil in a transformer or electrical apparatus and can identify the presence and concentration of at least two different gases substantially simultaneously and subsequently regenerate the sensing device.

SUMMARY OF THE INVENTION

The present invention fulfills this need by providing an on-line gas-in-oil monitoring apparatus and method that automatically extracts gases from the oil in an electrical apparatus and regenerates the sensing means. These gases are collected periodically, sampled, and analyzed for the presence and concentration of at least two pre-determined gases, such as hydrogen and carbon monoxide.

On-line gas-in-oil monitoring is comprised of two phases: separation of the gas from the oil, also known as permeation, and analysis of the gases, or detection. Gas separation from the oil may be accomplished by a permeation cell. Hydrogen and carbon monoxide gases present in the oil pass through a semipermeable membrane and are collected in a gas collection area. Every cycling period a sampling valve is opened allowing the collected gases to pass into a sensor housing containing the sensing means. The sensing means are sintered metal oxide semi-conductors with adsorbed oxygen that are predominantly sensitive to a predetermined gas. As the predetermined gas is passed over the sensing means, conductivity of the sensing means is altered due to a reaction between the oxygen and the reducing gas. The change in conductivity is proportional to the concentration of the gas in the sample. In a preferred embodiment, at least two sensing means are present in the sensor housing. Each sensing means is sensitive to a different reducing or combustible gas. Thus, the levels of at least two different gases in one analytical cycle may be determined. After the analytical cycle, the sensing means are regenerated for the next analytical cycle.

It is an object of the present invention to provide an on-line gas-in-oil monitoring apparatus for an electrical apparatus that can extract and determine the presence and concentration of more than one gas dissolved in the oil substantially simultaneously.

It is another object of the present invention to provide an inexpensive and efficient gas-in-oil monitoring apparatus.

It is a further object of the present invention to provide a method of determining the presence and concentration of reducing or combustible gases in oil.

It is a further object of the present invention to provide a gas-in-oil monitoring apparatus that is operatively associated with an oil-filled transformer that detects the presence and level of at least two gases dissolved in the oil.

It is an object of the present invention to provide metal oxide sensing means as gas detectors.

It is a further object of the present invention to provide a method of regeneration of the metal oxide sensing means after an analytical cycle.

BRIEF DESCRIPTION OF THE DRAWINGS

A full understanding of the invention can be gained from the following description of the preferred embodiments when read in conjunction with the accompanying drawings in which.

DESCRIPTION OF THE PREFERRED EMBODIMENTS

The on-line gas-in-oil monitoring apparatus separates gas from the oil and passes the gas to sensors where the presence and levels of gases may be determined.

The presence of a particular gas depends upon several factors, including the type of fault which produced the gas. Faults that produce gases-in-oil are arcing, corona, partial discharges, and hot spots due to overheating. Each of these faults produces a significant amount of free hydrogen. Therefore, a measurement of the hydrogen content in a transformer oil will provide a valid indication of fault history of the transformer. Carbon monoxide and/or carbon dioxide is produced when the primary insulation material of the transformer, cellulose is degraded.

Figure 1:
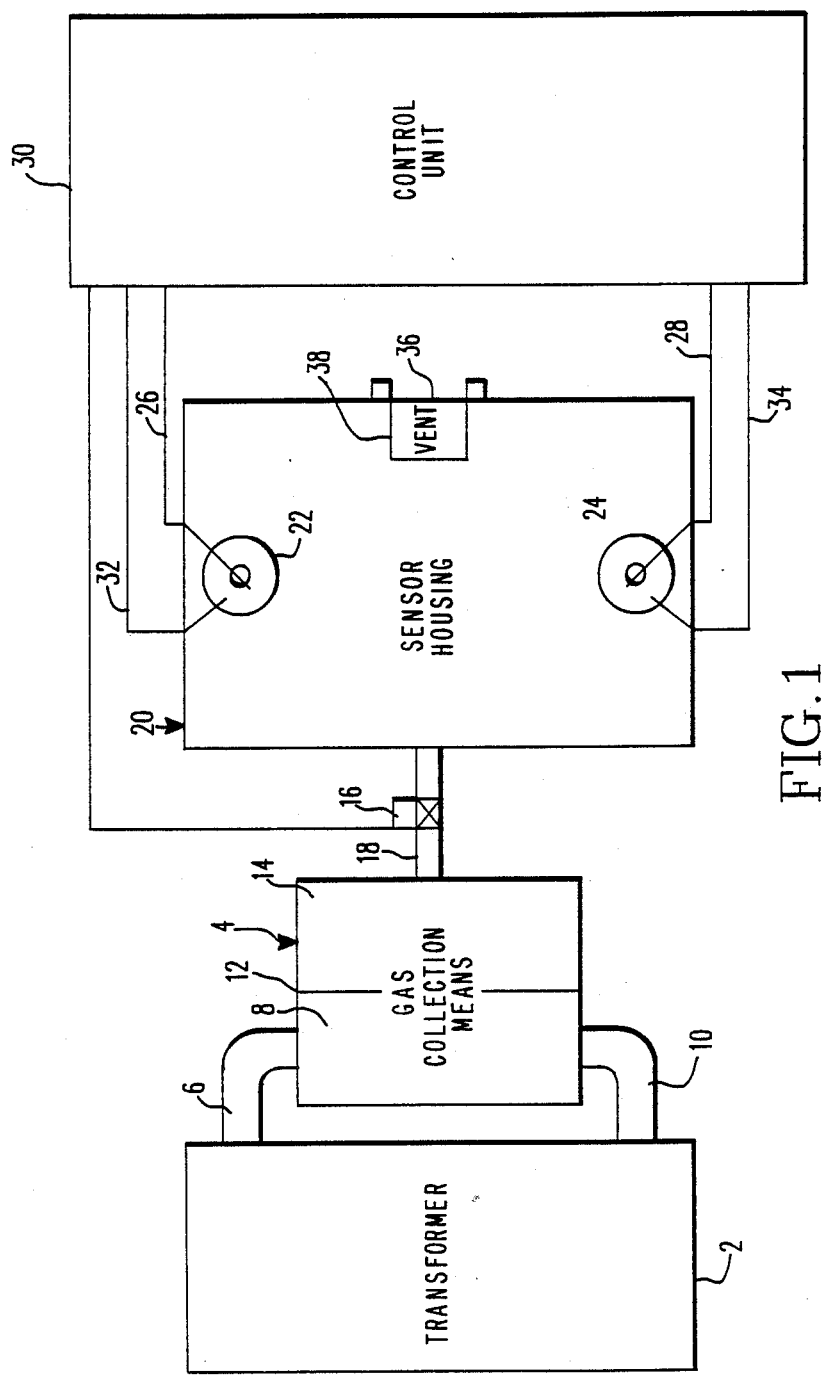
FIG. 1 a schematic diagram of the apparatus of the present invention.

FIG. 1 shows a transformer 2 operatively associated with the gas collection means 4. Oil is continually transported through a conduit 6 into a first chamber 8 of the gas collection means 4 and flows out of first chamber 8 through conduit 10 back into the transformer 2. The oil may be transported by pump or thermal syphon flow, for example.

A semipermeable membrane 12, preferably resistant to oil comprised of a polymeric material such as fluorosilicane or polytetrafluoroethylene, separates the first chamber 8 from the second chamber 14. The gases present in the oil move through the semipermeable membrane 12 into a second chamber 14. Oil is retained in the first chamber 8 and cycled back to the transformer 2.

A gas collection unit, such as is described by U.S. Pat. No. 3,866,460 or 4,058,373 may be used.

During the analytical cycle, the gases in chamber 14 are passed through pipe 18 through a valve means 16, preferably a solenoid valve means. The pipe 18 connects the second chamber 14 through the solenoid valve 16 to the sensor housing 20. The gases then pass into the sensor housing 20.

The sensor housing 20 contains a first sensing means 22 and a second sensing means 24. The first sensing means 22 is predominantly sensitive to a first predetermined gas. The second sensing means 24 is predominantly sensitive to a second predetermined gas. Preferably, these gases are reducing or combustible gases, such as hydrogen or carbon monoxide. Operatively associated with the first sensing means 22 is a first heating means 26. Operatively associated with the second sensing means 24 is a second heating means 28. The first and second heating means 26, 28 are operatively associated with a control unit 30.

The sensing means are metal oxide semi-conductors formed by sintering powdered tin (IV) oxide. The sintering process produces a large number of grain boundaries between individual crystals. The adsorption of oxygen forms potential barriers at these grain boundaries accompanied by a large reduction of semi-conductor conductivity. The amount of oxygen adsorbed at a fixed temperature by the metal oxide sensor maintains a constant conductivity because the partial pressure of oxygen and air remains virtually constant. When reducing or combustible gases are passed over the sensing means, the molecules of these gases are adsorbed so that the transfer of electrons is in the opposite direction to the oxygen reaction. This provides an increased density of electrons in the semi-conductor space charge layer and decreases potential barriers at the grain boundaries, resulting in increased sensing means conductivity in the presence of a reducing or combustible gas. The change in conductivity which may be measured as a change in output voltage, is proportional to the concentration of the respective gas.

The sensing means are sensitive to temperature changes so a constant temperature environment is desirable for the sensing means and a temperature controller and/or supplemental heater for the sensor housing are preferably employed. Optionally, thermal insulation such as, for example, Johns-Manville's Cera Blanket may be incorporated into the sensor housing in order to minimize temperature fluctuations in the sensor housing.

Operatively associated with the first sensing means is a first lead 32 which transmits any change in conductivity to the control unit 30. Operatively associated with the second sensing means 24 is a second lead 34, which is operatively associated with the control unit 30.

As the sample gases are passed over first and second sensing means 22, 24, any change in conductivity that occurs in these sensing means 22, 24 is sensed by the control unit 30 through the first and second leads 32, 34 respectively. The control unit 30 has detecting means which convert first and second signals received through said first and second leads into a display of the levels of the first and second predetermined gases.

In addition, there is a vent means 36 which is disposed in the sensor housing 20 in order to provide a supply of air through the sensor housing 20. Optionally, a desiccant means 38 may be associated with the vent means in order to minimize the amount of moisture present within the sensor housing and to eliminate any undesired gases from entering the chamber and altering the accuracy of the readings.

The control unit 30 converts the sensing means 22, 24 voltage output into concentrations of hydrogen and carbon monoxide. The control unit 30 also contains circuitry which initiates the automatic sampling through operation of the solenoid valve 16 and retains the current and peak hydrogen concentration readings. The control unit 30 may also generate alarm signals which alert the user when predetermined levels of the respective gases are present in the gas. The alarm may signal a power loss, a failure in the sensor circuitry, or a failure of the circuit providing heat to the sensor housing. The control unit also contains conventional circuitry for remote transmission of data.

After the sampled gases pass over the sensing means 22, 24, they escape through the vent means 36. In addition, any reactive cases, such as carbon dioxide from the carbon monoxide, are passed through the vent.

At the conclusion of a sampling period, the solenoid valve 16 is closed. The first and second sensing means 22, 24 are regenerated at this time by oxygen in the ambient air which enters sensor housing 20 through vent 36. During this period, oil from the transformer 2 continues to flow through the first chamber 8. All gases continue to pass through the semipermeable membrane 12 into the second chamber 14.

Identical sensing means may be used, with the temperature controlled to render each sensing, means sensitive to a particular gas. In the exemplary system, Figaro, Inc. Type 1817 tin (IV) oxide sensors are used. These sensors have integral heater wires. A heater voltage of about 2 volts raises the temperature of the sensor to about 120° C. while a heater voltage of about 5 volts produces a temperature of about 350° C.

The sensing means regenerate the oxygen lost in the reduction reaction in the presence of a regenerating gas such as ambient air or oxygen. As the sample gases are vented through the vent means, the regenerating gases, such as ambient air, enters into the sensor housing during the recovery period.

One sensing means may be predominantly sensitive to hydrogen. Temperature control or heating means provide a constant heat or voltage to the sensor. Preferably, the heater voltage is 4.50 to 6 volts in order to regenerate the oxygen level on the sensing means. The heater voltage remains constant. At the point the gases are admitted to the sensor housing, an analytic cycle begins, preferably for about an 8 minute period.

The other sensing means may be predominantly sensitive to carbon monoxide. Immediately after the analytical period, the heater voltage is raised to about 4.5 to 6 volts or about 350° C. for approximately 6 minutes in order to burn off any carbon monoxide that may be present on the sensing means for a first recovery period. Thereafter, a lower voltage is used, approximately 1.50 to 2.50 volts to provide a constant temperature of approximately 120° C. during the second recovery or regeneration period. It is preferred that the heater voltage be raised to approximately 4.50 to 6 volts for a short period of time, such as at least 45 minutes to an hour for a third recovery period in order to provide a proper reaction rate with the oxygen. This high heater voltage allows the sensor to recover to its original base line reading. The heater voltage is then lowered to approximately 2 volts for the analytical cycle. There is a 2 minute stabilization period during which the carbon monoxide sensing means is heated to approximately 2 volts. At the end of this period of time, the gases are admitted to the sensor housing and the analytical cycle begins. A voltage means provides a continuous measure of changes in conductivity and subtracts the base line reading from the voltage. This voltage is then compared to stored calibration data. At the end of the analytical cycle, the heater voltage is raised to approximately 5 volts for a period of about 6 minutes in order to burn off the carbon monoxide that has accumulated on the sensing means.

Figure 2:
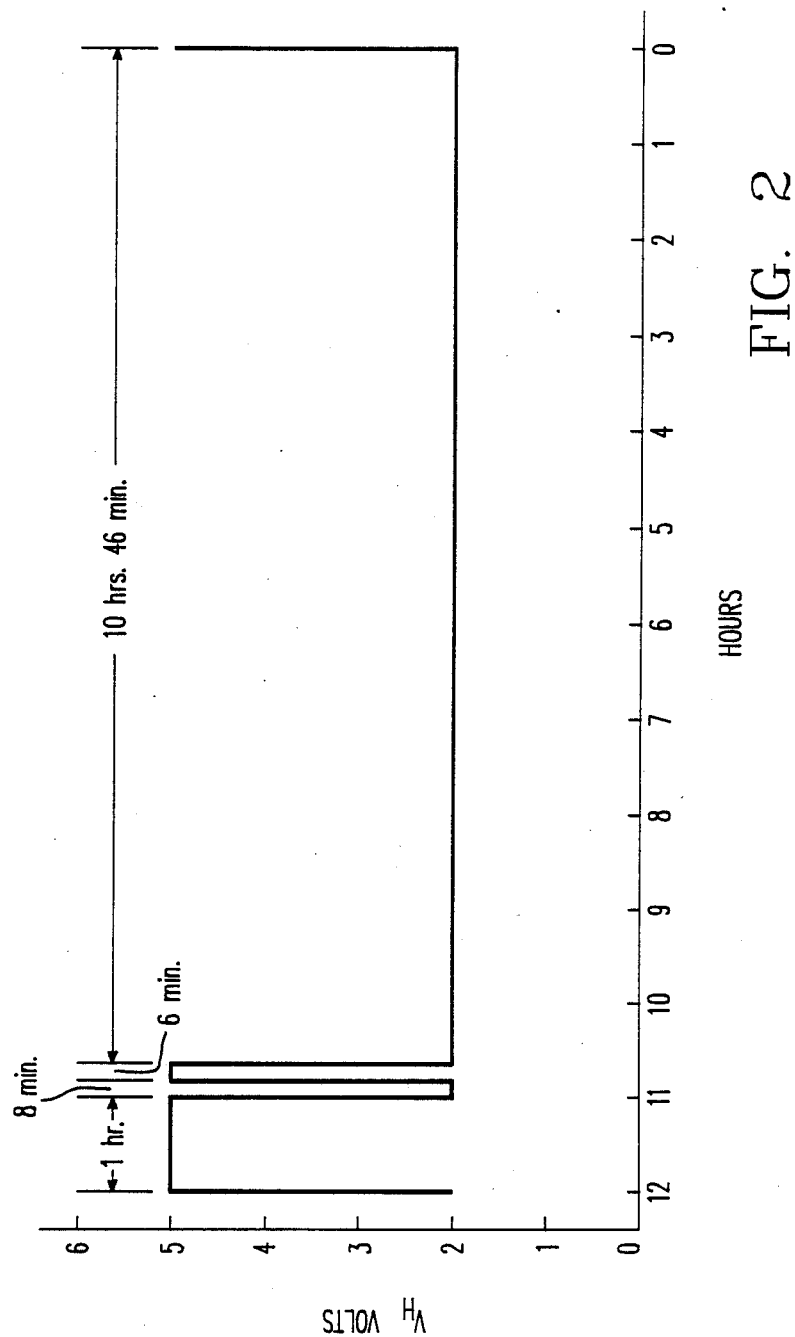
FIG. 2 a graph of the heater voltage of a sensor predominantly sensitive to carbon monoxide.

FIG. 2 shows the operating cycle for a carbon monoxide sensor. After the analytical cycle, there is a first regeneration period of approximately 6 minutes during which the heater voltage is raised to 5 volts. Thereafter, for the second recovery period about 10 hours and 46 minutes, the sensor is provided with a constant heater voltage of about 2 volts. The voltage is increased to approximately 4.50 to 6 volts, for the third recovery period for a period of about 45 minutes to an hour, in order to further regenerate the sensor. The heater voltage is then dropped to 2 volts, at the end of which period is signaled the beginning of the analytical period. The gas is admitted to the sensor housing and the analytical period extends for approximately 6 minutes, at a heater voltage of about 2 volts, during which time changes in conductivity are detected.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appending claims and any and all equivalents thereof.

What is claimed is:

1. An on-line gas-in-oil monitoring apparatus for oil-filled electrical apparatus which indicates substantially simultaneously the amount of at least two predetermined gases in the oil comprising:
   means for separating said predetermined gases from said oil;
   a sensor housing;
   means for periodically introducing a sample of said predetermined gases separated from said oil into said housing;
   a first gas sensing means disposed in said sensor housing which is predominantly sensitive to a first of said predetermined gases;
   a second gas sensing means disposed in said sensor housing which is predominantly sensitive to a second of predetermined gases;
   vent means for venting said sensor housing to the atmosphere for purging said predetermined gases from the sensor housing and to admit oxygen to said sensor housing to resensitize said sensing means to said predetermined gases;
   control means which are responsive to a change in conductivity of said first and second sensing means in response to the presence of said first and second predetermined gases respectively, and generate an indication of the levels of the first and second predetermined gases;
   said first sensing means is predominantly sensitive to carbon monoxide;
   said second sensing means is predominantly sensitive to hydrogen;
   said sensing means are sintered metal oxide semiconductors with adsorbed oxygen;
   heating means which provide heat or voltage to said sensing means;
   said heating means provides a first heating voltage to said first sensing means to heat said second sensing means to a temperature which renders said first sensing means sensitive to the first of said predetermined gases; and
   a second heating voltage to said second sensing means to heat said second sensing means to a temperature which renders said second sensing means sensitive to the second of said predetermined gases.

2. The apparatus of claim 1
   wherein said means for separating said predetermined gases from said oil comprises
   a first chamber through which said oil flows;
   a diffusion membrane which defines a portion of said first chamber;
   said diffusion membrane being constructed of a material which permits the predetermined gases contained in the oil to diffuse through said membrane;
   a second chamber which is disposed generally adjacent to said diffusion membrane into which said predetermined gases diffuse through said diffusion membrane; and
   wherein said means for periodically introducing a sample of said predetermined gases into said housing includes a valve means for allowing a sample of said predetermined gases to flow from said second chamber into said sensor housing.

3. A method of providing on-line measurement of a sample of at least two predetermined gases in oil substantially simultaneously comprising:
   separating said predetermined gases from said oil;
   providing a sensor housing with at least two sensing means comprised of sintered metal oxide semi-conductors with adsorbed oxygen disposed therein;
   periodically introducing a sample of said predetermined gases into said sensor housing whereby said sensing means are exposed to said predetermined gases;
   measuring the conductivity of said sensing means; and
   regenerating one of said sensing means predominantly sensitive to the presence of hydrogen by heating said sensing means in the presence of oxygen for a recovery period;
   regenerating the other of said sensing means predominantly sensitive to the presence of carbon monoxide by
   heating said sensing means at a higher temperature for a first recovery period;

heating said sensing means at a lower temperature for a second recovery period; and heating said sensing means at a higher temperature for a third recovery period.

4. The method of claim 3 including controlling the temperature of said sensing means by means of heating means to provide a means for sensitizing the sensing means to said predetermined gases.

5. The method of claim 3 including heating the sensing means to different temperatures to sensitize said sensing means to the levels of two different gases respectively.

6. The method of claim 3 including providing a recovery period of at least about 11 hours during which time period said sensor is exposed to oxygen.

7. The method of claim 3 including heating said sensing means predominantly sensitive to hydrogen to about 350° C. during an analytical period.

8. The method of claim 7 including heating said sensing means to a temperature of about 350° C. for said recovery period.

9. The method of claim 7 including providing an analytical period of about 6 minutes.

10. The method of claim 3 including heating said sensing means at a temperature of about 350° C. for said first recovery period.

11. The method of claim 3 including heating said sensing means at a temperature of about 120° C. for said second recovery period.

12. The method of claim 3 including heating said sensing means at a temperature of about 350° C. for said third recovery period.

13. The method of claim 10 including providing a first recovery period of at least about 6 minutes.

14. The method of claim 11 including providing a second recovery period of at least about 10 hours.

15. The method of claim 12 including providing a third recovery period of at least about 45 minutes.

16. The method of claim 14 including providing a second recovery period of about 10 hours and 46 minutes.

17. The method of claim 15 including providing a third recovery period of about 1 hour.

18. The method of claim 3 including providing an analytical period of about 6 minutes.

19. The method of claim 18 including heating said sensing means to a temperature of about 120° C. during said analytical period.

* * * * *